(12) United States Patent
Vogel et al.

(10) Patent No.: US 9,132,141 B2
(45) Date of Patent: Sep. 15, 2015

(54) ADMINISTRATION OF ERITORAN OR PHARMACEUTICALLY ACCEPTABLE SALTS THEREOF TO TREAT ORTHOMYXOVIRUS INFECTIONS

(71) Applicant: University of Maryland, Baltimore, Baltimore, MD (US)

(72) Inventors: Stefanie Vogel, Columbia, MD (US); Kari Ann Shirey, Cockeysville, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 13/783,580

(22) Filed: Mar. 4, 2013

(65) Prior Publication Data

US 2013/0261076 A1 Oct. 3, 2013

Related U.S. Application Data

(60) Provisional application No. 61/616,784, filed on Mar. 28, 2012, provisional application No. 61/771,339, filed on Mar. 1, 2013.

(51) Int. Cl.
*A61K 31/7024* (2006.01)
*A61K 45/06* (2006.01)

(52) U.S. Cl.
CPC ............. *A61K 31/7024* (2013.01); *A61K 45/06* (2013.01)

(58) Field of Classification Search
None
See application file for complete search history.

(56) References Cited

U.S. PATENT DOCUMENTS

| 2007/0072824 A1 | 3/2007 | Kawano et al. |
| 2008/0095786 A9* | 4/2008 | McShane .................... 424/184.1 |
| 2010/0015125 A1 | 1/2010 | Crispe et al. |
| 2011/0201569 A1 | 8/2011 | Ehrentraut et al. |

FOREIGN PATENT DOCUMENTS

| WO | WO 2007/053455 A2 | 5/2007 |
| WO | WO 2007/139150 A1 | 12/2007 |

OTHER PUBLICATIONS

Ho, Y. et al "Prognostic factors for fatal adult influenza pneumonia" J. Infect. (2009) vol. 58, pp. 439-445.*
Christ et al., *E5531, a pure endotoxin antagonist of high potency*, 268(5207) Science 80-3 (1995).
Cooke et al., *LPS antagonism reduces graft-versus-host disease and preserves graft-versus-leukemia activity after experimental bone marrow transplantation*, 107(12) Journal of Clinical Investigations 1581-9 (2001).
Czeslick et al., *E5564 (Eritoran) inhibits lipopolysaccharide-induced cytokine production in human blood monocytes*, 55(11) Inflammation Research 511-5 (2006).
Ehrentraut et al., *In vivo Toll-like receptor 4 antagonism restores cardiac function during endotoxemia*, 36(6) Shock 613-20 (2011).
Fang et al., *An oligodeoxynucleotide capable of lessening acute lung inflammatory injury in mice infected by influenza virus*, 415(2) Biochemical and Biophysical Research Communications 342-7 (2011).
Hawkins et al., *Inhibition of endotoxin response by synthetic TLR4 antagonists*, 4(11) Current Topics in Medicinal Chemistry 1147-71 (2004).
Haynes et al., *Involvement of toll-like receptor 4 in innate immunity to respiratory syncytial virus*, 75(22) Journal of Virology 10730-7 (2001).
Kalil et al., *Influence of severity of illness on the effects of eritoran tetrasodium (E5564) and on other therapies for severe sepsis*, 36(4) Shock 327-31 (2011).
Kaneko et al., *Disposition of a synthetic analogue of lipid A (E5564) in rats*, 33(3) Xenobiotica 323-39 (2003).
Kaneko et al., *LPS binding protein does not participate in the pharmacokinetics of E5564*, 10(3) Journal of Endotoxin Research 185-94 (2004).
Kawata et al., *Anti-endotoxin activity of a novel synthetic lipid A analog*, 392 Progress in Clinical and Biological Research 499-509 (1995).
Kim et al., *PKA-I holoenzyme structure reveals a mechanism for cAMP-dependent activation*, 130(6) Cell 1071-82 (2007).
Kitazawa et al., *Therapeutic approach to regulate innate immune response by Toll-like receptor 4 antagonist E5564 in rats with D-galactosamine-induced acute severe liver injury*, 24(6) Journal of Gastroenterology and Hepatology 1089-94 (2009).
Kitazawa et al., *Salvage effect of E5564, Toll-like receptor 4 antagonist on d-galactosamine and lipopolysaccharide-induced acute liver failure in rats*, 25(5) Journal of Gastroenterology and Hepatology 1009-12 (2010).

(Continued)

*Primary Examiner* — Leigh Maier
(74) *Attorney, Agent, or Firm* — Buchanan Ingersoll & Rooney PC

(57) ABSTRACT

The present invention is directed to methods for treating orthomyxovirus infections comprising administering to a subject an effective amount of a compound of formula (I)

or a pharmaceutically acceptable salt thereof.

37 Claims, 18 Drawing Sheets

(56) References Cited

OTHER PUBLICATIONS

Liang et al., *Pharmacokinetics of E5564, a lipopolysaccharide antagonist, in patients with impaired hepatic function*, 43(12) Journal of Chemical Information and Computer Science 773-8 (2003).
Lien et al., *A novel synthetic acyclic lipid A-like agonist activates cells via the lipopolysaccharide/toll-like receptor 4 signaling pathway*, 276(3) Journal of Biological Chemistry 1873-80 (2001).
Ludwig S., *Targeting cell signalling pathways to fight the flu: towards a paradigm change in anti-influenza therapy*, 64(1) Journal of Antimicrobial Chemotherapy 1-4 (2009).
Mullarkey et al., *Inhibition of endotoxin response by e5564, a novel Toll-like receptor 4-directed endotoxin antagonist*, 304(3) Journal of Pharmacology and Experimental Therapeutics 1093-102 (2003).
Ondiveeran et al., *Drug evaluation: E-5564*, 7(6) iDrugs 582-90 (2004).
Raja et al., *Eritoran: the evidence of its therapeutic potential in sepsis*, 2(3) Core Evidence 199-207 (2007).
Rossignol et al., *Endotoxin in Health and Disease*, 699-717 (Helmut Brade et al., eds. 1st ed., 1999).
Rossignol et al., *Antagonism of in vivo and ex vivo response to endotoxin by E5564, a synthetic lipid A analogue*, 8(6) Journal of Endotoxin Research 483-8 (2002).
Rossignol et al., *Safety, pharmacokinetics, pharmacodynamics, and plasma lipoprotein distribution of eritoran (E5564) during continuous intravenous infusion into healthy volunteers*, 48(9) Antimicrobial Agents and Chemotherapy 3233-40 (2004).
Rossignol et al., *Continuous pharmacodynamic activity of eritoran tetrasodium, a TLR4 antagonist, during intermittent intravenous infusion into normal volunteers*, 14(6) Innate Immunity 383-94 (2008).
Savov et al., *Toll-like receptor 4 antagonist (E5564) prevents the chronic airway response to inhaled lipopolysaccharide*, 289(2) American Journal of Physiology—Lung Cellular and Molecular Physiology L329-37 (2005).
Shaw M., *The host interactome of influenza virus presents new potential targets for antiviral drugs*, 21(6) Genome Research 358-69 (2011).
Shiozaki et al., *Syntheses of glucose derivatives of E5564-related compounds and their LPS-antagonistic activities*, 341(7) Carbohydrate Research 811-22 (2006).
Solomon et al., *Effective dosing of lipid A analogue E5564 in rats depends on the timing of treatment and the route of Escherichia coli infection*, 193(5) Journal of Infectious Disease 634-44 (2006).
Sun et al., *Inhibition of Corneal Inflammation by the TLR4 Antagonist Eritoran Tetrasodium (E5564)*, 50(3) Investigative Ophthalmology & Visual Science 1247-1254 (2009).
Tidswell et al., *Phase 2 trial of etitoran tetrasodium (E5564), a toll-like receptor 4 antagonist, in patients with severe sepsis*, 38(1) Critical Care Medicine 72-83 (2010).
Visintin et al., *Pharmacological inhibition of endotoxin responses is achieved by targeting the TLR4 coreceptor, MD-2*, 175(10) Journal of Immunology 6465-72 (2005).
Wenzel et al., *Septic shock—evaluating another failed treatment*, 366(22) New England Journal of Medicine 2122-4 (2012).
Yang et al., *Examination of chlorpromazine and other amphipathic drugs on the activity of lipopolysaccharide antagonists, E5564 and E5531*, 6(6) Journal of Endotoxin Research 447-52 (2000).
Zhou et al., *Physiologic, biochemical, and imaging characterization of acute lung injury in mice*, 172(3) American Journal of Respiratory and Critical Care Medicine 344-51 (2005).
Zughaier S., *Neisseria meningitidis capsular polysaccharides induce inflammatory responses via TLR2 and TLR4-MD-2*, 89(3) Journal of Leukocyte Biology 469-80 (2011).
International Report on Patentability and Written Opinion for PCT/US2013/028856, dated Oct. 9, 2014.
Chandran et al., "TLR2 Engagement on Dendritic Cells Promotes High Frequency Effector and Memory CD4 T Cell Responses," J. Immunol, 183:7832-41 (2009).
Cole et al., "Macrophage Proinflammatory Response to *Francisella tularenis* Live Vaccine Strain Requires Coordination of Multiple Signaling Pathways," J. Immunol., 180:6885-91 (2008).
Cole et al., "Role of TLR signaling in *Francisella tularensis*-LPS-induced, antibody-mediated protection against *Francisella tularensis* challenge," J. Leukocyte Biology, 90:787-97 (Oct. 2011).
Imai et al., "Identification of Oxidative Stress and Toll-like Receptor 4 Signaling as a Key Pathway of Acute Lung Injury," Cell, 133:235-49 (2008).
Nhu et al., "Novel Signaling Interactions Between Proteinase-Activated Receptor 2 and Toll-like Receptors In Vivo and In Vitro," Mucosal Immunology, 3(1):29-39 (2010).
Rallabhandi et al., "Analysis of TLR4 Polymorphic Variants: New Insights into TLR4/MD-2/CD14 Stoichiometry, Structure, and Signaling," J. Immunol., 177:322-32 (2006).
Shirey et al., "Control of RSV-induced lung injury by alternatively activated macrophages is IL-4Rα-, TLR4-, and IFN-β-dependent," Mucosal Immunology, 3(3):291-300 (2010).
Shirey et al., "*Francisella tularensis* Live Vaccine Strain Induces Macrophage Alternative Activation as a Survival Mechanism," J. Immunol. 181:4159-67 (2008).
Shirey et al., "The anti-tumor agent, 5,6-dimethylxanthenone-4-acetic acid (DMXAA), induces IFN-β-mediated antiviral activity in vitro and in vivo," J. Leukocyte Biology, 89:351-57 (Mar. 2011).
Teijaro et al., "Costimulation Modulation Uncouples Protection from Immunopathology in Memory T Cell Responses to Influenza Virus," J. Immunol. 182:6834-43 (2009).
International Search Report and Written Opinion for PCT/US2013/028856, dated May 16, 2013.
"Universal Influenza Vaccines Meeting Summary," National Institute of Allergy and Infectious Diseases, National Institutes of Health, U.S. Food and Drug Administration, Jun. 19-20, 2012, pp. 1-18.
Cheng et al., "Two Years after Pandemic Influenza A/2009/H1N1: What Have We Learned?," Clinical Microbiology Reviews, 25(2):223-263 (Apr. 2012).
Andonegui et al., "Mice that exclusively express TLR4 on endothelial cells can efficiently clear a lethal systemic Gram-negative bacterial infection," J. Clin. Invest., 119:1921-1930 (2009).
Eisai News Release, "Phase III Study for Severe Sepsis Treatment Eritoran (E5564) Does Not Meet Primary Endpoint," No. 11-08, Jan. 25, 2011, 2 pages.
Genetic Engineering & Biotechnology News, "Phase III Study Finds Eisai's Eritoran Fails to Reduce Mortality in Severe Sepsis," Gen News Highlights: Jan. 25, 2011, 1 page.
Opal et al., "Effect of Eritoran, an Antagonist of MD2-TLR4, on Mortality in Patients with Severe Sepsis The ACCESS Randomized Trial," JAMA, 309(11):1154-1162 (Mar. 20, 2013) Corrected in Apr. 8, 2013.

\* cited by examiner

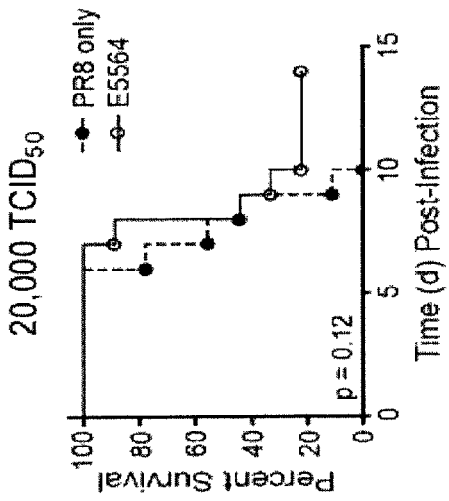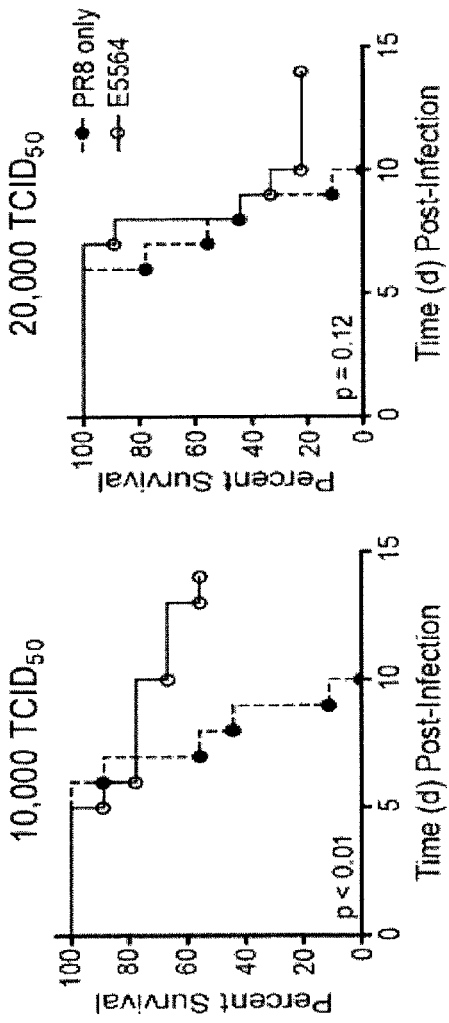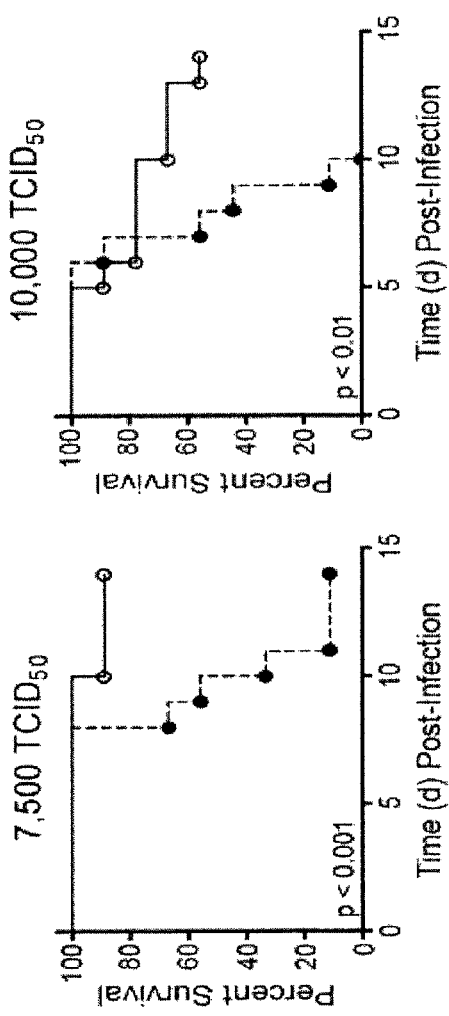

ADMINISTRATION OF ERITORAN OR PHARMACEUTICALLY ACCEPTABLE SALTS THEREOF TO TREAT ORTHOMYXOVIRUS INFECTIONS

CROSS REFERENCE TO RELATED APPLICATIONS

This application claims priority under 35 U.S.C. §119 to U.S. Provisional Patent Application No. 61/616,784, filed on Mar. 28, 2012, and U.S. Provisional Patent Application No. 61/771,339, filed on Mar. 1, 2013; the content of each is hereby expressly incorporated by reference in their entireties for all purposes and each is assigned to the assignee hereof.

STATEMENT REGARDING FUNDING

This invention was made with Government support of Grant No. AI18797, awarded by the National Institutes of Health. The Government has certain rights in this invention.

BACKGROUND OF THE INVENTION

In the Northern hemisphere, viral epidemics cause up to 80% of all respiratory illnesses. The most common infections are caused by six viral groups: rhinovirus (RVs), respiratory syncytial virus, influenza virus, parainfluenza virus, corona virus, and adenovirus.

Influenza is a contagious respiratory illness caused by a group of viruses that are part of the virus family orthomyxoviridae. Influenza viruses are significant human respiratory pathogens that cause both seasonal, endemic infections and periodic, unpredictable pandemics. The worst pandemic on record, in 1918, killed approximately 50 million people worldwide. Human infections caused by H5N1 highly pathogenic avian influenza viruses have raised concerns about the emergence of another pandemic. Influenza viruses cause epidemic respiratory illness every winter in most countries on the planet. Influenza often begins with cold-like symptoms and progresses to involve the lungs. Most patients develop a chronic cough that can last for weeks. Pneumonia can develop and is a common cause of death among more susceptible people. It can cause mild to severe illness, and at times can lead to death. Certain groups, such as the very young, the very old and the immunocompromised, are at higher risk for contracting the virus and developing serious complications from infection.

Previous attempts to treat influenza infection focused on neuraminidase inhibitors to prevent the release of new infectious virus and halt viral replication. Other attempts focused on adamantane M2 ion channel blockers, such as amantadine and rimantadine. However, problems arose with viral resistance to treatment. Influenza viruses constantly mutate. In addition, antigenic changes take place each year in the annual dominant influenza strain. As a result, vaccines generated to stimulate immune responses to viral antigens must be prepared yearly. Annual influenza shots are recommended for all persons at risk, but the vaccines are based on last year's virus strains with no guarantee that they will protect against newly emergent viruses. During the winter flu season, people who develop respiratory illness require therapeutic treatment to reduce their ability to spread the disease. Thus, a need exists for new therapeutic drugs that limit the effects of influenza virus infection by targeting aspects of the host immune response.

SUMMARY OF THE INVENTION

The present teachings relate, at least in part, to the discovery that a compound of formula (I) or pharmaceutically acceptable salts thereof, can be used to treat orthomyxovirus infections in an infected subject. More specifically, the present invention relates to the discovery that eritoran or a pharmaceutically acceptable salt thereof can be used to treat subjects infected with influenza to limit the effects and duration of infection. The compound of formula (I) has been shown, for example, to reduce influenza virus-induced cytokine production, reduce influenza virus-associated pathology, and prevent death in mice.

In one embodiment the invention pertains to a method for treating a patient infected with influenza virus comprising administering to the infected patient a therapeutically effective amount of eritoran or a pharmaceutically acceptable salt thereof.

In another embodiment the invention pertains to a method for treating a patient infected with an orthomyxovirus comprising administering to the infected patient a composition comprising an active ingredient and a pharmaceutically acceptable carrier wherein the active ingredient comprises eritoran or a pharmaceutically acceptable salt thereof.

In another embodiment the invention pertains to a method for mitigating influenza-induced disease comprising administering to the infected animal a therapeutically effective amount of a TLR4 antagonist, wherein the TLR4 antagonist comprises eritoran or a pharmaceutically acceptable salt thereof.

In another embodiment the invention pertains to a method further comprising administering to the infected patient a therapeutically effective amount of an antiviral compound.

In another embodiment the invention pertains to a method wherein the infected patient is administered a therapeutically effective amount of eritoran or a pharmaceutically acceptable salt thereof following testing positive for the presence of influenza infection.

In another embodiment the invention pertains to a method wherein the infected patient tested for the presence of influenza infection using PCR, rt-PCR, direct antigen detection tests, virus isolation in cell culture, or combinations thereof.

In another embodiment the invention pertains to a method further comprising causing a decrease in influenza-induced cytokine mRNA levels in the infected patient.

In another embodiment the invention pertains to a method further comprising causing a decrease in influenza-induced cytokine mRNA levels in the infected patient wherein the cytokines comprise TNF-α, IL-1β, IL-6, COX-2, IL-12 p40, KC, IL-10, IL-5, TGF-β or combinations thereof.

In another embodiment the invention pertains to a method further comprising causing a decrease in influenza-induced interferon-beta or interferon gamma mRNA levels in the infected patient.

In another embodiment the invention pertains to a method wherein the infected patient is administered a therapeutically effective amount of eritoran or a pharmaceutically acceptable salt thereof following the onset of clinical symptoms, wherein the clinical symptoms comprise cough, fever, pneumonia or combinations thereof.

In another embodiment the invention pertains to a method wherein the composition is administered by one of the routes comprising intravenous administration, intraperitoneal administration, intramuscular administration, intracoronary administration, intraarterial administration, intradermal administration, subcutaneous administration, transdermal delivery, intratracheal administration, subcutaneous administration, intraarticular administration, intraventricular administration, inhalation, intracerebral, nasal, naval, oral, intraocular, pulmonary administration, impregnation of a catheter, by suppository and direct injection into a tissue, or systemically absorbed topical or mucosal administration.

In another embodiment the invention pertains to a method wherein the effects of administering eritoran or pharmaceutically acceptable salts thereof cause a decrease in viral titers in the infected patient.

In another embodiment the invention pertains to a method wherein the infected patient is administered a therapeutically effective amount of eritoran or a pharmaceutically acceptable salt thereof in a range of from between about 1 μg to about 240 mg, per dose.

In another embodiment the invention pertains to a method wherein the patient is infected with an orthomyxovirus selected from the group comprising influenza A, influenza B, influenza C or combinations thereof.

BRIEF DESCRIPTION OF FIGURES

FIGS. 4A, 4B, and 4C show eritoran-mediated protection is overcome by increased influenza dosages.

FIGS. 5A and 5B show eritoran treatment reduces viral titers in infected subjects.

DETAILED DESCRIPTION

Figure 1A:
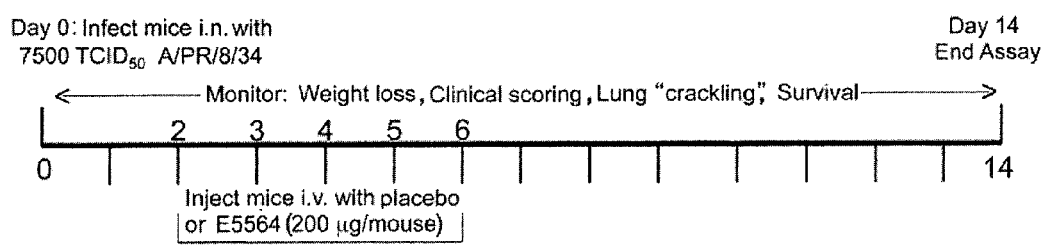
FIGS. 1A, 1B, and 1C show eritoran protects mice from lethal influenza challenge.

The innate immune system is the first line of defense against invading microorganisms. Immune competent cells, such as macrophages, dendritic cells, neutrophils, and endothelial cells recognize pathogen-associated molecular patterns (PAMPS) on the surface of pathogens, as diverse as Gram-positive and Gram-negative bacteria, viruses, fungi, and Mycoplasma. The toll-like receptors (TLRs) are a family of closely related receptors that trigger cellular innate immune signaling pathways in response to discreet stimuli defined by conserved PAMPS. To date, ten different human TLRs have been identified. One of those TLRs, TLR3, has previously been shown to induce production anti-viral cytokines in response to double-stranded RNA produced during influenza infection. TLR4 is typically associated with activating innate immune signaling in response to lipopolysaccharide (LPS) produced during infection by Gram-negative bacteria. It was previously shown, however, that TLR4-deficient mice were strongly resistant to infection by a mouse-adapted strain of influenza, A/PR/8/34. (Q. M. Nhu et al., Mucosal Immunology, Vol. 3, No. 1: 29-39, (2010)). TLR4 mutant mice have also been shown to display natural resistance to acid-induced acute lung injury. (Y. Imai et al., Cell, 133: 235-249 (2008)). However, there are no studies indicating whether inhibition of TLR4 in infected subjects may provide potential therapeutic effects following virus infection.

Eritoran (also known as E5564, compound 1287, SGEA or (α-D-Glucopyranose, 3-O-decyl-2-deoxy-6-O-[2-deoxy-3-O-[(3R)-3-methoxydecyl]-6-O-methyl-2-[[(-11Z)-1-oxo-11-octadecenyl]amino]-4-O-phosphono-β-D-glucopyranosyl]-2-[(1,3-dioxotetradecyl)amino]-1-(dihydrogen phosphate)) has previously been shown to be an effective antagonist of TLR4. This drug is described as compound 1 in U.S. Pat. No. 5,681,824, which is incorporated herein by reference for its description of compound 1 and methods of making same. Eritoran, has the structure of formula (I):

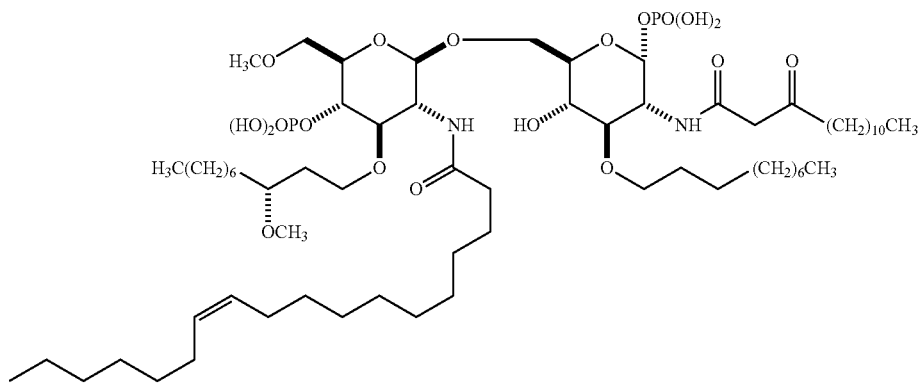

and may be provided as one of a number of pharmaceutically acceptable salts. The compound of formula I may be prepared in the form of a micelle, as described in U.S. Pat. No. 6,906,042, which is incorporated herein by reference in its entirety for the description of such micelles and methods for preparing same.

The present invention is directed to methods of treating respiratory virus infections and more particularly, for treating infections by orthomyxoviruses. In another embodiment, the invention provides a method of treating influenza virus infection in an animal by administering to the animal an inhibitor of TLR4. One embodiment of the present invention pertains to methods to treat influenza virus infection in an animal by administering to the animal a therapeutically effect amount of eritoran or a pharmaceutically acceptable salt thereof.

Another embodiment of the present invention pertains to methods to treat influenza virus infection by reducing viral replication in an infected host by inhibiting TLR4.

Compounds suitable for use with the methods of the present invention include inhibitors of TLR4. In a preferred embodiment of the present invention, methods of the present invention are practiced using eritoran or a pharmaceutically acceptable salt thereof to inhibit TLR4 signaling. Eritoran is a synthetic lipid A analog that interferes with LPS signaling through TLR4. Eritoran and pharmaceutically acceptable salts thereof competitively inhibit LPS to bind the hydrophobic pocket of MD-2. When bound, eritoran or a pharmaceutically acceptable salt thereof prevents TLR4 dimerization and intracellular signaling.

In one embodiment of the present invention, treatment with eritoran or a pharmaceutically acceptable salt thereof decreases influenza induced pathology. Symptoms associated with respiratory virus infection, and more particularly associated with influenza infection, include among others cough, fever and pneumonia. Frequently, influenza infection leads to cellular damage to the lungs. According to the present invention, treatment of an infected subject with eritoran or a pharmaceutically acceptable salt thereof dramatically reduces cellular damage in the lung tissue. In addition, treatment with eritoran or a pharmaceutically acceptable salt thereof in the days following infection according to the invention disclosed herein may also lead to reduced systemic effects of influenza infection. In one embodiment of the invention, influenza-induced increases in liver enzyme levels are reduced by treatment with eritoran or a pharmaceutically acceptable salt thereof.

Acute respiratory viral infection (especially from the H5N1 subtype influenza virus) results in the expression of a multitude of cytokines capable of affecting the lungs, and subsequent damage to alveoli and lung tissue results in the lethality seen in more severe influenza infections, especially those fatalities among young healthy adults. Excessive inflammation triggered by the virus infection can result in significant pathology. In another embodiment of the present invention, TLR4 is antagonized to decrease expression of influenza-induced cytokine RNA expression in influenza infected subjects. In one embodiment of the present invention, the TLR4 antagonist, eritoran or a pharmaceutically acceptable salt thereof may result in a decrease in the production of influenza-induced cytokine RNA expression in infected subjects. Without wishing to be bound to any particular theory, it is believed that influenza viruses infect cells and activate cellular signaling pathways that drive the production of inflammatory cytokines. According to the present invention, the TLR4 pathway may be targeted by eritoran to reduce production of inflammatory cytokines in subjects infected with influenza viruses. In one embodiment of the invention, eritoran or a pharmaceutically acceptable salt thereof is used to reduce influenza-induced expression of interferon-beta RNA expression in subjects infected with influenza. In another embodiment of the invention, eritoran or a pharmaceutically acceptable salt thereof is used to reduce influenza-induced expression of interferon-gamma RNA expression in subjects infected with influenza. In another embodiment of the invention, eritoran treatment of subjects infected with influenza does not reduce influenza-induced expression of interferon-alpha 4. In another embodiment of the invention, eritoran treatment of subjects infected with influenza does not reduce influenza-induced expression of interferon-delta 2. In some embodiments of the present invention, eritoran treatment of infected subjects may be used to decrease influenza-induced expression of specific species of interferon without affecting the expression of other species of interferon. Methods of the present invention may also be used for decreasing TLR4-mediated expression of TNF-$\alpha$, IL-1$\beta$, IL-6, COX-2, IL-12 p40, KC, IL-10, IL-5 and TGF-$\beta$.

In yet another embodiment of the present invention, the effects of eritoran or a pharmaceutically acceptable salt thereof result in decreased influenza virus replication in infected subjects compared to untreated subjects. While not wishing to be bound to any particular theory, it is believed that eritoran or a pharmaceutically acceptable salt thereof's inhibitory effects on TLR4 signaling produces a cellular environment that is less suitable to virus growth.

Methods of the present invention may be used to treat any strain of influenza infection. According to one embodiment of the present invention, the methods pertain to treatment for influenza A strains. According to one embodiment of the present invention, the methods pertain to treatment for influenza B strains. According to one embodiment of the present invention, the methods pertain to treatment for influenza C strains. In addition, methods of the present invention may also be used to treat other orthomyxoviruses.

According to one embodiment of the invention, the method of the present invention includes detecting the presence of influenza infection in the respiratory specimens of a subject. A number of different laboratory diagnostic tests can be used for detecting the presence of influenza viruses in respiratory specimens, including direct antigen detection tests, virus isolation in cell culture, detection of influenza-specific RNA by real-time reverse transcriptase-polymerase chain reaction (rRT-PCR) or others.

According to the methods of the present invention, treatment may begin within up to about 6 days following infection with influenza or at the onset of clinical symptoms. According to a preferred embodiment of the present invention, treatment may begin within up to about 4 days following infection with influenza. According to a more preferred embodiment of the present invention, treatment may begin within up to about 2 days following infection with influenza. The present invention relates to methods of treating subjects suffering from a virus infection, or more specifically subjects suffering from influenza virus infection.

Administration of eritoran or a pharmaceutically acceptable salt thereof according to the present invention is typically carried out over the course of several days. The efficacy of the methods of the present invention have been shown to increase in a dose dependent manner, with higher dosages providing more effective treatment for infection. A single dose may be administered from between 1 μg to approximately 240 mg. In one embodiment, a single dose may be administered from between 1 μg to approximately 50 mg. In another embodiment a single dose may be administered from between 1 μg to approximately 70 mg. In yet another embodiment, a single dose may be administered from between 1 μg to approximately 90 mg. In yet another embodiment, a single dose may be administered from between 1 μg to approximately 125 mg. In yet another embodiment, a single dose may be administered from between 1 μg to approximately 150 mg. In yet another embodiment, a single dose may be administered from between 1 μg to approximately 200 mg. The appropriate amounts of which can be determined by one of skill in the art according to the characteristics of the infected subject and the preferred route of administration. In the methods of the invention, eritoran or a pharmaceutically acceptable salt thereof may also be administered to patients by intravenous infusion over a period of 12-100 hours, e.g., 60-80 or 72 hours. The infusion dosage rate may vary, for example, 0.001-0.5 mg/kg body weight/hour, e.g., 0.01-0.2 mg/kg/hour or 0.03-0.1 mg/kg/hour. The infusion of eritoran or a pharmaceutically acceptable salt thereof can, if desired, be preceded by a bolus injection of eritoran or a pharmaceutically acceptable salt thereof, which can be given at a dosage of 0.001-0.5 mg/kg body weight. The total amount of eritoran or a pharmaceutically acceptable salt thereof administered to a patient can be, for example, 50-600 mg of drug, e.g., 150-500 mg, by infusion over a period of 60-80 hours. In another embodiment, eritoran or a pharmaceutically acceptable salt thereof may be administered to patients by intravenous infusion over a period of 1-10 hours for a total daily dose of between 1-20 mg. For example, the total amount of eritoran or pharmaceutically acceptable salt thereof administered to a patient may be between about 1 and about 10 mg in a daily dose, administered by intravenous infusion over a period of up to 5 hours. In one embodiment, the total amount of eritoran or a pharmaceutically acceptable salt thereof administered to a patient is 5 mg in a daily dose, administered by intravenous infusion over a period of about 1 hour. In one embodiment, the total amount of eritoran or a pharmaceutically acceptable salt thereof administered to a patient is 5 mg in a daily dose, administered by intravenous infusion over a period of about 4 hours. The quantity and method of administration may vary during the course of treatment. For example, a patient may first receive eritoran or a pharmaceutically acceptable salt thereof by intravenous injection during the initial stage of infection to be followed by inhalation methods of administration for a series of days, including up to about 14 days post-infection.

Appropriate frequency of administration may also be determined by one of skill in the art. For example, the drug may be administered 1-4 times per day, preferably 2-4 times per day. Administration may be continuous over a selected period of time or may be in a series of spaced doses. Administration of the drug may continue until symptoms of the infection have disappeared. In some cases, it may be preferable to continue administration for several days. In one embodiment, administration may continue for several days after clinical symptoms of infection have disappeared. It will be understood that specific dosage ranges and pharmaceutical formulations may vary according to the method of administration and the specific physical characteristics of the subject being treated.

In order to more clearly and concisely describe the subject matter of the claims, the following definitions are intended to provide guidance as to the meaning of terms used herein.

As used herein, the articles "a" and "an" mean "one or more" or "at least one," unless otherwise indicated. That is, reference to any element of the present invention by the indefinite article "a" or "an" does not exclude the possibility that more than one of the element is present.

Values and ranges are recited in collection with various embodiments of the present invention, e.g., amount of a compound of formula (I) present in a composition. It is to be understood that all values and ranges which fall between the values and ranges listed are intended to be encompassed by the present invention unless explicitly stated otherwise.

The term "effective amount" of a compound refers to a sufficient amount of the compound that provides a desired effect but with no- or acceptable-toxicity. This amount may vary from subject to subject, depending on the species, age, and physical condition of the subject, the severity of the disease that is being treated, the particular compound used, its mode of administration, and the like. A suitable effective amount may be determined by one of ordinary skill in the art.

"Treatment", "treat", or "treating" as used herein, are defined as the application or administration of a therapeutic agent to a subject, or to an isolated tissue or cell line from a subject. The subject generally has a disease or disorder, a symptom of disease or disorder or a predisposition toward a disease or disorder (e.g., influenza). Specifically as used herein, treatment is directed at subjects already infected with a virus, such as influenza, as opposed to subjects that have not yet been infected. The purpose of treatment is generally to cure, heal, alleviate, relieve, remedy, ameliorate, or improve such disease, disorder, or symptoms. "Treated", as used herein, refers to the disease or disorder being cured, healed, alleviated, relieved, remedied, ameliorated, or improved.

Compounds suitable for use with the methods of the present invention are administered in therapeutically effective dosages. The term "therapeutically effective amount" is used to indicate an amount of an active compound, or pharmaceutical agent, that elicits the biological or medicinal response indicated. This response may occur in a tissue, system (animal including human) that is being sought by a researcher, veterinarian, medical doctor or other clinician.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al., describe pharmaceutically acceptable salts in detail in J. Pharmaceutical Sciences, 66: 1-19 (1977). The salts can be prepared in situ during the final isolation and purification of the compounds taught herein, or separately by reacting a free base or free acid function with a suitable reagent, as described generally below. For example, a free base function can be reacted with a suitable acid. Furthermore, where the compounds taught herein carry an acidic moiety, suitable pharmaceutically acceptable salts thereof may, include metal salts such as alkali metal salts, e.g., sodium or potassium salts; and alkaline earth metal salts, e.g., calcium or magnesium salts. Sodium salts of compounds within the scope of formula I are described, for example, in U.S. patent application Ser. No. 12/516,082 and U.S. Patent Application Publication No. 2008/0227991. Examples of pharmaceutically acceptable, nontoxic acid addition salts are salts formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. In some embodiments, the compound of formula (I) is a sodium salt, e.g., a tetrasodium salt.

The term "subject" refers to an animal, preferably a mammal, and most preferably a human, who is the object of treatment, observation or experiment. The mammal may be selected from the group consisting of mice, rats, hamsters, gerbils, rabbits, guinea pigs, dogs, cats, sheep, goats, cows, horses, giraffes, platypuses, primates, such as monkeys, chimpanzees, and apes. In some embodiments, the subject is a human.

As used herein, the terms "antagonist" and "inhibitor" refer to molecules or compounds that inhibit the action of a "native" or "natural" molecules or compounds.

In some embodiments, the compounds described herein are administered systemically. As used herein, "systemic administration" refers to any means by which the compounds described herein can be made systemically available. In some embodiments, systemic administration encompasses intravenous administration, intraperitoneal administration, intramuscular administration, intracoronary administration, intraarterial administration (e.g., into a carotid artery), intradermal administration, subcutaneous administration, transdermal delivery, intratracheal administration, subcutaneous administration, intraarticular administration, intraventricular administration, inhalation (e.g., aerosol), intracerebral, nasal, naval, oral, intraocular, pulmonary administration, impregnation of a catheter, by suppository and direct injection into a tissue, or systemically absorbed topical or mucosal administration. Mucosal administration includes administration to the respiratory tissue, e.g., by inhalation, nasal drops, ocular drop, etc.; anal or vaginal routes of administration, e.g., by suppositories; and the like. In some embodiments, the compounds described herein are administered intravenously. In other embodiments, the compounds described herein are administered orally. In some embodiments, the compounds described herein may be administered intravenously one to five times a week. In some other embodiments, the compounds described herein may be administered orally one or more times a day (e.g., once a day, twice a day or three times a day).

Pharmaceutical formulations suitable for use with the present invention may also include excipients, preservatives, pharmaceutically acceptable carriers and combinations thereof. the term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols. The compositions can additionally include lubricating agents such as talc, magnesium stearate, and mineral oil; wetting agents; emulsifying agents; suspending agents; preserving agents such as methyl-, ethyl-, and propyl-hydroxy-benzoates; pH adjusting agents such as inorganic and organic acids and bases; sweetening agents; and flavoring agents.

Methods of the present invention may also be used in combination with other treatment regimes. For example, one embodiment of the present invention pertains to combination therapy in which eritoran or a pharmaceutically acceptable salt thereof is used in combination with one or more antiviral drugs known in the art. Currently, there are two main classes of antiviral drugs used against influenza: neuraminidase inhibitors, such as zanamivir and oseltamivir, or inhibitors of the viral M2 protein, such as amantadine and rimantadine. The present invention pertains to methods of treatment that combine eritoran or a pharmaceutically acceptable salt thereof with neuraminidase inhibitors, inhibitors of the viral M2 protein or combinations thereof.

EXAMPLES

Mice

Six to 8-week old, WT C57BL/6J mice were purchased (The Jackson Laboratory, Bar Harbor, Me.). All animal experiments were conducted with institutional approval.

Virus

Mouse-adapted H1N1 influenza A/PR/8/34 virus ("PR8") (ATCC, Manassas, Va.) was grown in the allantoic fluid of 10-day old embryonated chicken eggs as previously described (J. R. Tejaro et al., J. Immunol., 182: 634-6843 (2009)) and was provided by Dr. Donna Farber (Columbia University). Non-adapted human influenza virus strain A/Wuhan359/95 (H3N2) was obtained and grown as previously described (Ottolini et al., J. Gen. Virol., 86:2523-2830 (2005)). Non-adapted human influenza strain A/California/07/2009 strain (human pandemic H1N1) was kindly provided by Ted Ross (U. Pittsburgh).

Virus Challenge and Treatments

C57BL/6J WT mice were infected with mouse-adapted influenza virus, strain A/PR/8/34 (PR8; ~7500 $TCID_{50}$, i.n., 25 µl/nares; this dose was found in preliminary experiments to kill ~90% of infected mice). Two days after infection, mice received either placebo or eritoran (200 µg/mouse in 100 ml sterile water, i.v.) daily (from Day 2 to Day 6). Where indicated, eritoran was administered 3 h prior to infection for 5 successive days. In some experiments, some groups of mice were treated with eritoran starting at day 4 or day 6 post-infection and treated for 5 or 3 consecutive days, respectively. Mice were monitored daily for survival, weight loss, and clinical signs of illness (e.g., lethargy, piloerection, ruffled fur, hunched posture, rapid shallow breathing) for 14 days. A clinical score ranging from 0 (no symptoms)-5 (moribund) was ascribed to each mouse daily. In some experiments, mice were euthanized at the indicated times post-infection to harvest serum for liver enzyme levels or lungs for analysis of gene expression, lung pathology, or viral titers.

Eritoran Protects Mice from Lethal Influenza Challenge

Figure 1B:
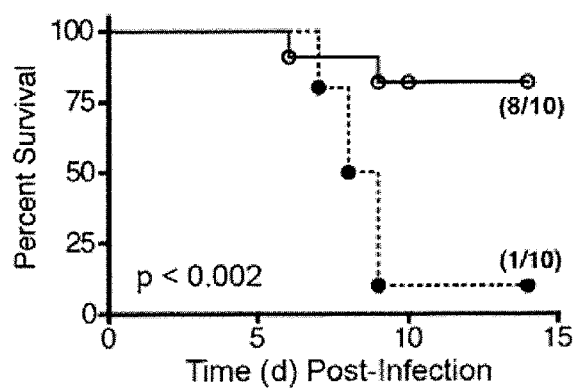
Figure 1C:
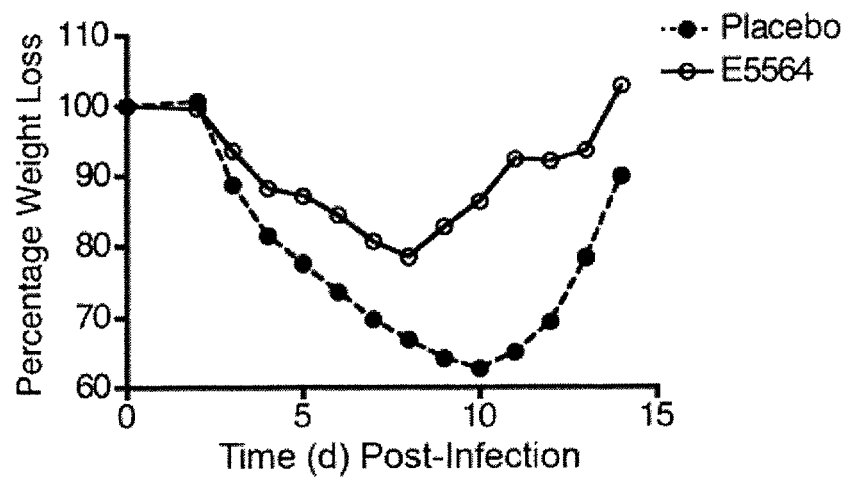

C57BL/6J mice were infected with mouse-adapted influenza virus strain A/PR/8/34 (PR8). FIG. 1a illustrates the initial protocol. On "Day 0," 6-8 week old female mice were infected intranasally (i.n.) with a dose of PR8 that was determined to kill ~90% of mice (7500 $TCID_{50}$). Starting 2 days after infection, the mice received either eritoran (200 µg/mouse in 100 µl sterile water, i.v.) or placebo (provided by Eisai) once daily for 5 successive days (Day 2 to Day 6). Each mouse was weighed and clinical symptoms (e.g., lethargy, piloerection, ruffled fur, hunched posture, rapid shallow breathing, audible rattling) were scored daily for 2 weeks. Eritoran and its corresponding placebo (provided by Eisai Inc.; Andover, Mass.) were prepared at 2.33 mg/ml in sterile, endotoxin-free water and diluted for injection in sodium bicarbonate-buffered 5% dextrose water. As shown in FIG. 1b, survival was monitored daily. FIG. 1c shows weight measurements over the 14 day period. Results represent two separate experiments, each with 5 mice/treatment/experiment.

Eritoran-Mediated Treatment for Influenza is Time Dependent

Figure 2A:
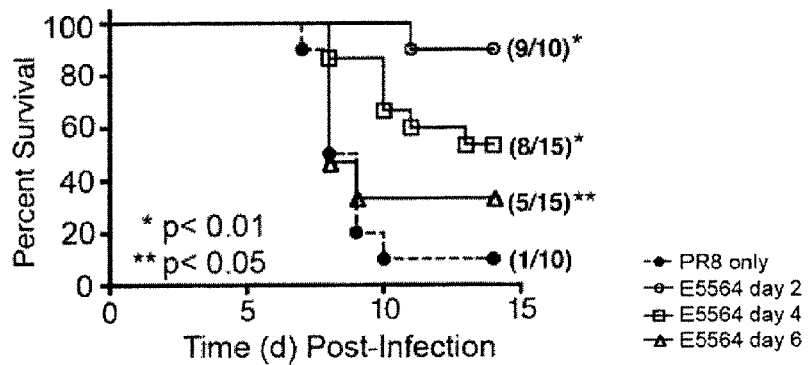
FIGS. 2A, 2B, and 2C show eritoran-mediated treatment for influenza is time dependent.
Figure 2B:
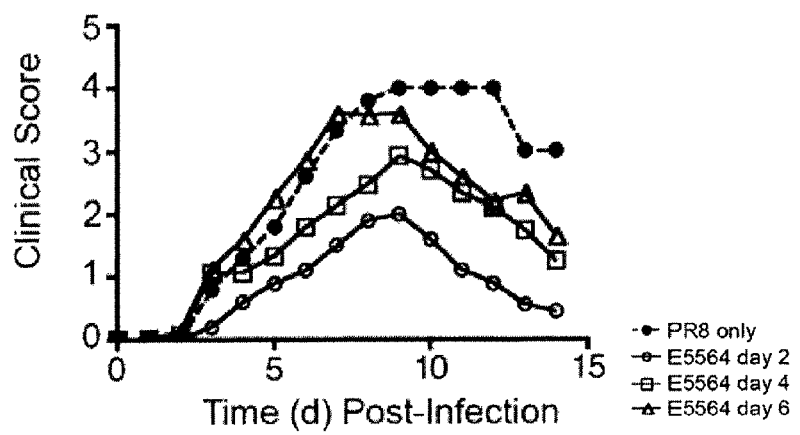
Figure 2C:
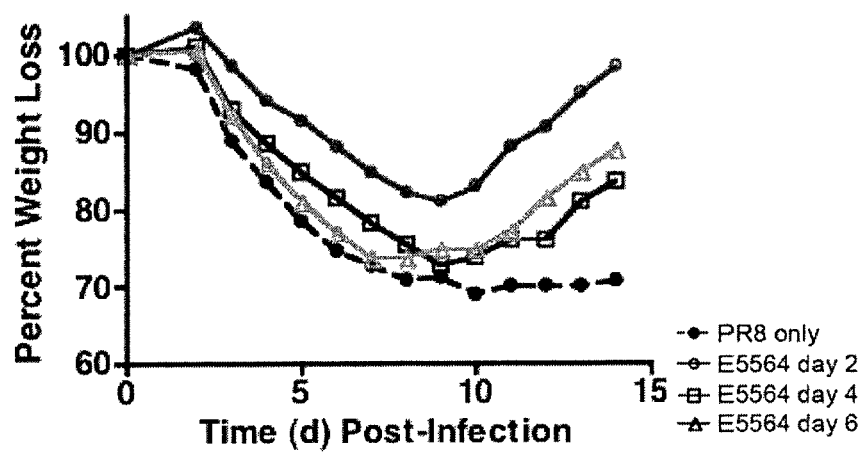

Mice were infected with PR8 (PR8; ~7500 $TCID_{50}$, i.n). Mice were treated or not treated with eritoran beginning on days 2, 4, or 6 post-infection. Mice receiving eritoran on days 2 or 4 received five treatments on consecutive days. Mice receiving eritoran on day 6 received treatment for three consecutive days. Additional treatments were not possible for the day 6 mice due to the severity of the infection. FIG. 2a shows the percent survival (days 2 and 4, $p<0.01$, day 6, $p\leq0.05$) for mice treated beginning at days 2, 4, and 6 compared to untreated mice. FIG. 2c shows the percent weight loss for mice treated beginning at days 2, 4, and 6 compared to untreated mice. FIG. 2b shows the clinical scores (based on defined criteria, e.g., ruffled fur, lethargy, etc.) for each subset of mice (M. D. Tate, et al., Respiratory Research, 9:57, 1-13 (2008)). Results represent combined results from two to three separate experiments with 5 mice per treatment per experiment.

Eritoran-Mediated Protection from Influenza is Dose Dependent

Figure 3A:
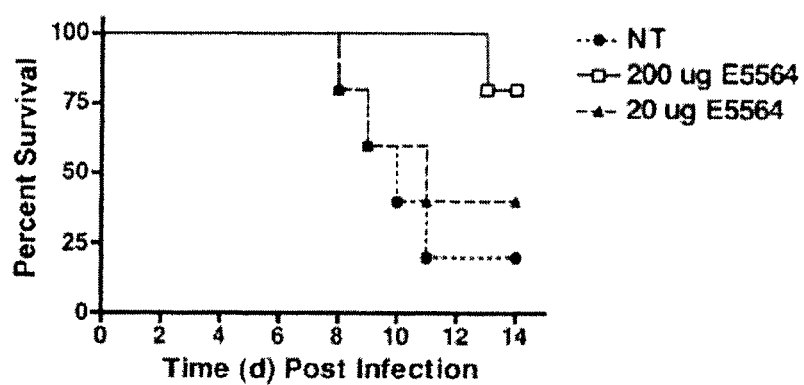
FIGS. 3A and 3B show eritoran-mediated protection from influenza is dose-dependent.
Figure 3B:
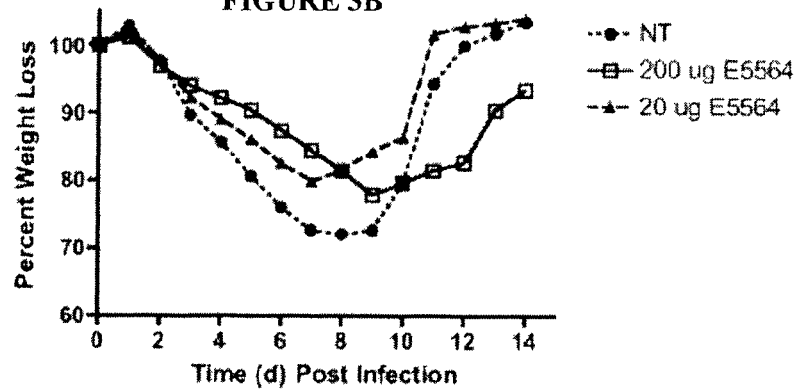

Mice were infected (i.n.) with 7500 $TCID_{50}$ PR8. Mice were left untreated or treated with eritoran (200 µg/mouse or 20 µg/mouse) starting on day 2 for 5 consecutive days. As shown in FIGS. 3a and 3b, mice infected with 7500 $TCID_{50}$ and treated with 200 µg/mouse eritoran exhibited improved survival (4/5 mice survived) compared to mice that received only 20 µg/mouse (4/10 survived) with ⅕ surviving in the untreated group. These are the results from a single experiment.

Eritoran-Mediated Protection is Overcome by Increased Influenza Dosages

Figure 4D:
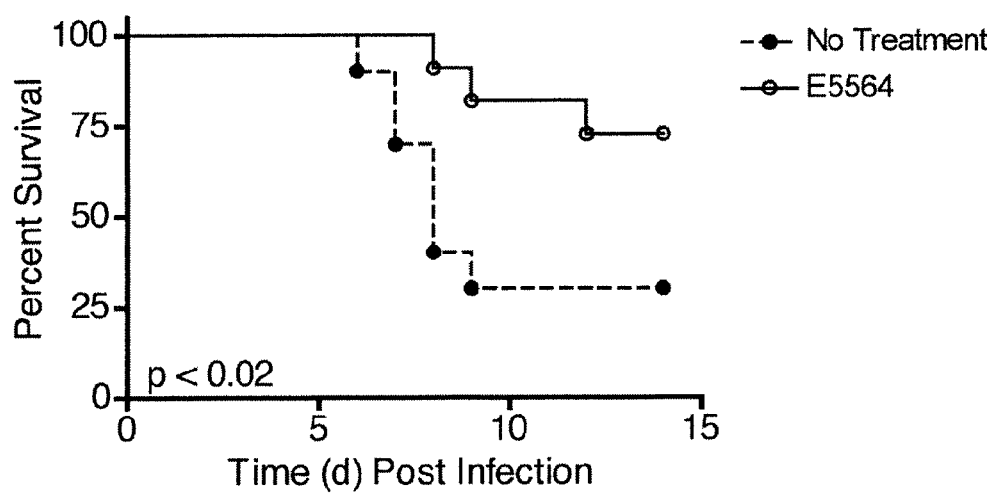
FIG. 4D shows eritoran protection against 2009 pH1N1.

Mice were infected (i.n.) with either 7500 $TCID_{50}$, 10,000 $TCID_{50}$, or 20,000 $TCID_{50}$ PR8. Mice were left untreated or treated with eritoran beginning on day 2 post-infection. Mice infected with 7500 $TCID_{50}$ and treated with eritoran exhibited a 88% survival rate (FIG. 4a), while those infected with 10,000 (FIG. 4b) or 20,000 (FIG. 4c) $TCID_{50}$ and treated with eritoran exhibited 55% and 22% survival rates, respectively. Results represent combined results from two separate experiments with 4-5 mice/treatment group/experiment. Mice were infected (i.n.) with $10^7$ $TCID_{50}$ A/California/07/2009 H1N1 (FIG. 4d). Mice were left untreated or treated with eritoran starting on day 2 post-infection and treated for 5 consecutive days. Mice were monitored for survival 14 days. These are the combined results from 2 separate experiments, each with 4-5 animals/treatment group/experiment.

Eritoran Treatment Reduces Viral Titers in Infected Subjects

Mice were infected (i.n.) with 50 µl of PR8 (~7500 $TCID_{50}$/mouse). Treated mice received 100 µl of eritoran (200 µg/mouse) i.v. starting on day 2 post-infection. Virus titers were obtained from the supernatants of lung homogenates of PR8-infected mice and expressed at $TCID_{50}$/ml as described previously (Shirey K A et al., J. Leukoc. Biol., 89(3):351-7 (2011)). FIGS. 5a and 5b show lungs harvested on days 2, 4, 6 and 7 post-infection. FIG. 5a represents the combined results of two experiments with 5 mice/group/experiment. Eritoran treatment resulted in a statistically significant decrease in lung viral titers. As can be seen in FIG. 5b, the lung viral titers were further decreased in the eritoran treatment group on day 7.

Eritoran Treatment Mitigates Influenza-Induced Lung Pathology

Figure 6A:
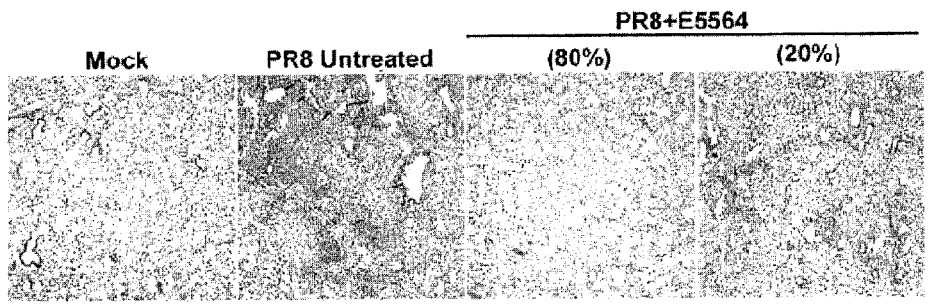
FIGS. 6A through 6E show eritoran treatment mitigates influenza-induced lung pathology.
Figure 6B:
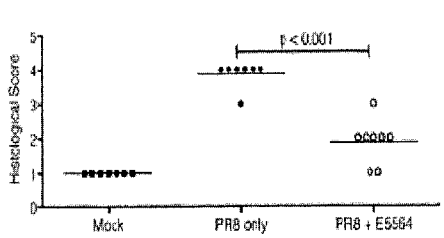
Figure 6C:
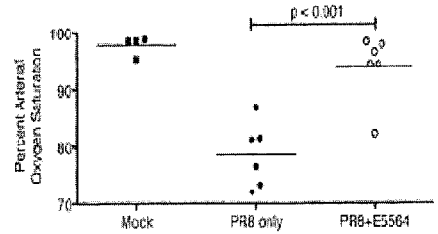

Mice were infected i.n. with 50 µl of PR8 (~7500 $TCID_{50}$/mouse). Mice were then injected i.v. with 100 µl of eritoran (200 µg/mouse) starting on day 2 post-infection. Mice were then sacrificed on day 7 post-infection (day 2 post-eritoran treatment) and lungs harvested for lung pathology (4 mice/treatment group). Murine lungs were inflated and perfused and fixed with 4% PFA. Fixed sections (8 µm) of paraffin-embedded lungs were stained with hematoxylin and eosin (H&E). Slides were randomized, read blindly, and examined for tissue damage, necrosis, apoptosis, and proinflammatory cellular infiltration. FIG. 6a shows images of lung pathology at 10×. PR8+ eritoran lungs was nearly normal in ~80% of lung sections; however, ~20% of lung sections showed inflammatory infiltrates, although to a much lesser extent than seen in PR8-infected control mice. These results are supported by blinded histological scoring (FIG. 6b). Pulse oximetry measurements were performed to confirm these observations. By day 6 post-infection, the oxygen saturation levels observed between mock-infected and PR8-infected mice demonstrated a significant oxyhemoglobin desaturation to 78%, suggesting a functional consequence of the alveolar injury demonstrated histologically (FIG. 6c).

Figure 6D:
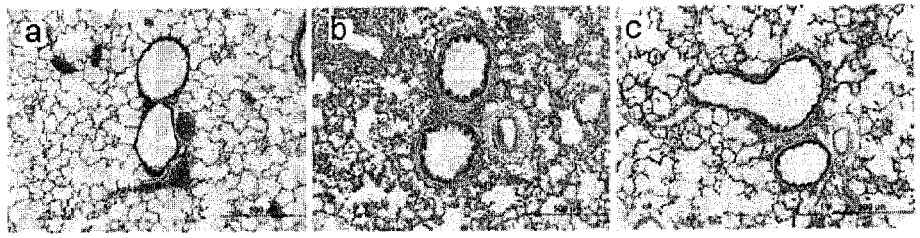
Figure 6E:
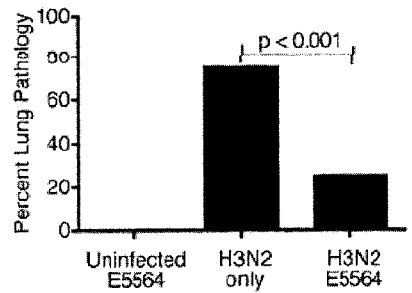

To determine whether the therapeutic effect extends to other animal models of human influenza infection, infection experiments were performed in cotton rats. A/Wuhan/359/95 (H3N2), a human unadapted strain of influenza, replicates in lung of cotton rats on day 1 and produces peak lung pathology on day 4 post-infection (FIG. 6d, panel b and FIG. 6e, H3N2 only). Animals treated with eritoran post-H3N2 challenge showed significant reduction in lung pathology on day 4 (FIG. 6d, panel c and FIG. 6e, H3N2/E5564).

Eritoran Treatment Reduces Influenza-Induced Cytokine Production

Figure 7A:
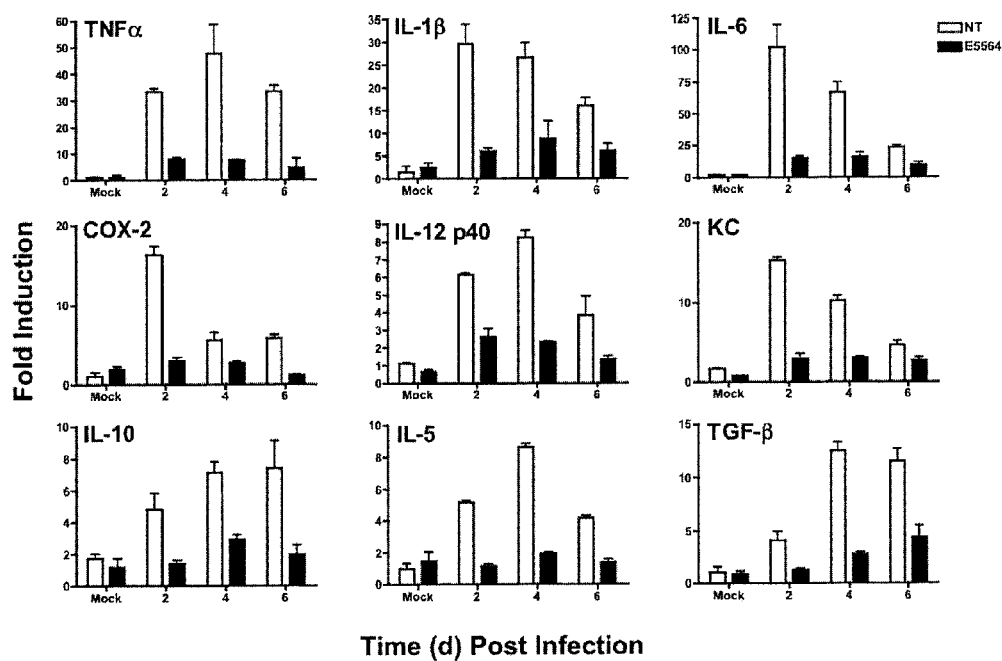
FIGS. 7A, 7B, and 7C show eritoran treatment reduced influenza-induced cytokine production.
Figure 7B:
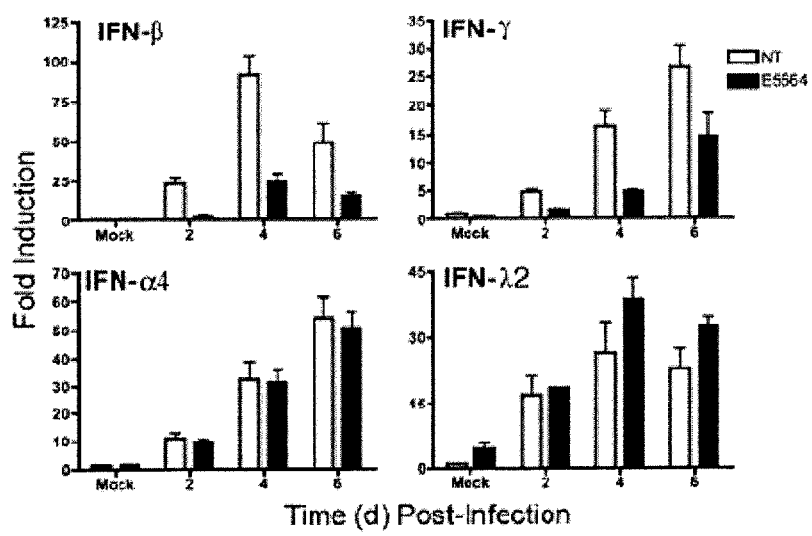
Figure 7C:
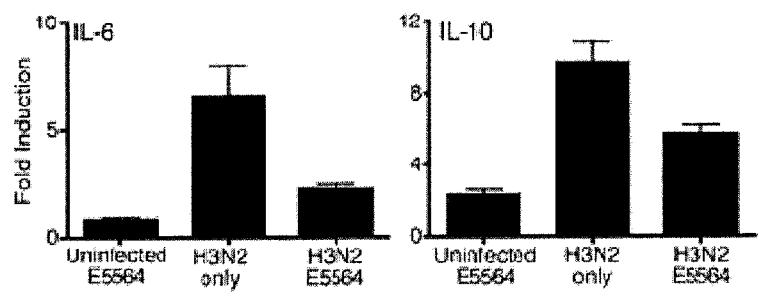

Mice infected i.n. with 50 µl of PR8 (~7500 $TCID_{50}$/mouse). Mice injected i.v. with 100 µl of eritoran (200 µg/mouse) starting on day 2 post-infection. Mice were sacrificed on days 2, 4, and 6 post-infection and lungs harvested for total RNA. Total RNA isolation and real-time PCR were performed as previously described (Shirey K A et al., J. Immunol., 181(6):4159-67 (2008); Shirey K A et al., Mucosal Immunology, 3(3):291-300 (2010)). Levels of mRNA for specific genes are reported as relative gene expression normalized to mock-infected lungs. Results are derived from two experiments (4 mice/treatment group). Eritoran-treated mice showed significantly reduced cytokine gene expression at each time point (FIG. 7a). Eritoran-treated mice showed variable levels of interferon production compared to control mice depending on the species of interferon mRNA measured (FIG. 7b). Eritoran treatment in cotton rats infected with the non-adapted human Wuhan H3N2 strain showed decreased lung expression of IL-6 and IL-10 (FIG. 7c).

Figure 8A:
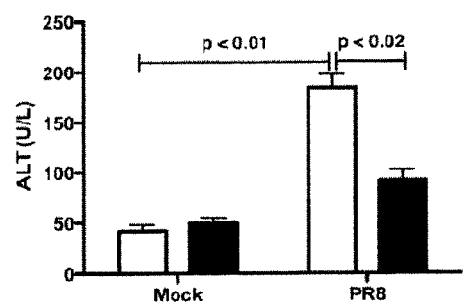
FIGS. 8A and 8B show eritoran treatment results in lower levels of influenza-induced liver enzyme levels.
Figure 8B:
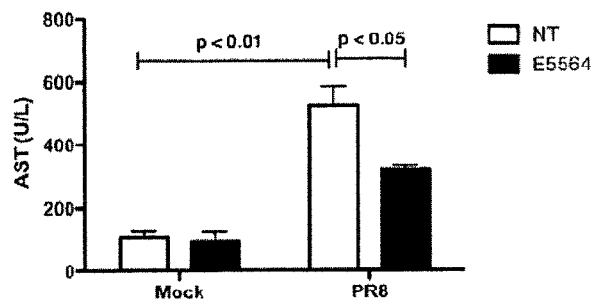

Eritoran Treatment Results in Lower Levels of Influenza-Induced Liver Enzyme Levels Mice infected i.n. with 50 µl of PR8 (~7500 $TCID_{50}$/mouse). Mice injected i.v. with 100 µl of eritoran (200 µg/mouse) starting on day 2 post-infection. Serum was collected on day 7 from C57BL/6J WT mice that were either mock-infected with saline or infected with PR8 and were either left untreated or were treated with eritoran starting on day 2 post-infection. Alanine aminotransaminase (ALT) and aspartate aminotransaminase (AST) were measured (Siemens Healthcare Diagnostics, Ltd.). As shown in FIGS. 8a and 8b, mice treated with eritoran expressed lower levels of liver enzymes post-infection. Data represent 2 separate experiments with 4 mice per treatment per experiment.

Eritoran Inhibits Influenza-Induced Oxidized Host Phospholipids (OxPL)

Figure 9:
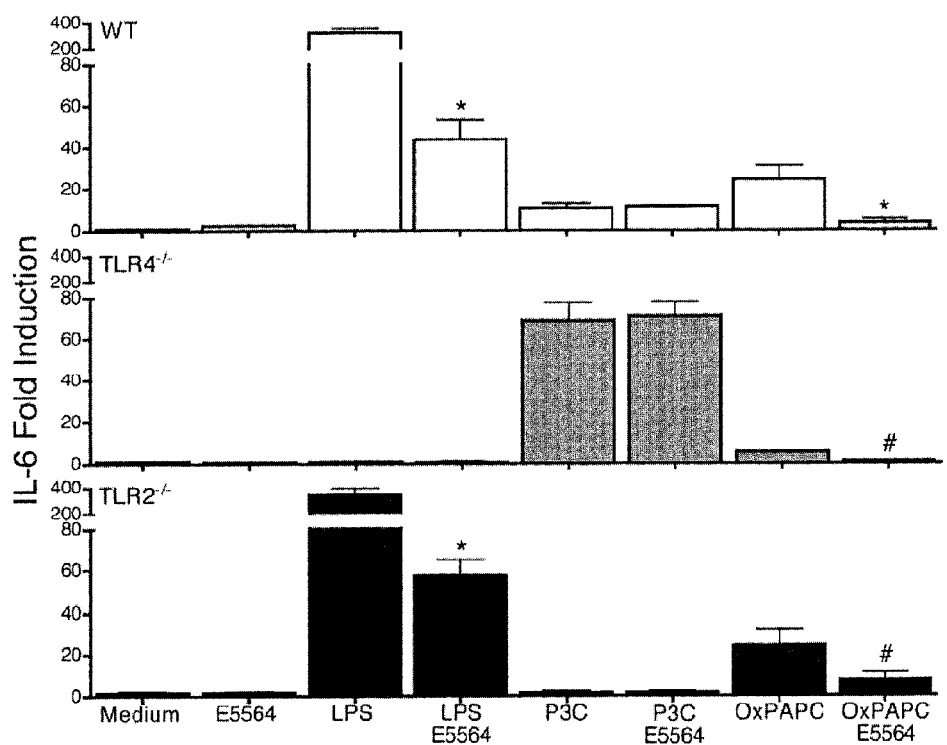
FIG. 9 shows eritoran treatment inhibits TLR4-dependent cell activation by OxPAPC.

Wild-type C57BL/6J, TLR4$^{-/-}$, and TLR2$^{-/-}$ peritoneal macrophages were pretreated with eritoran (10 ng/mL) for 1 hour and then treated with medium alone, LPS (20 ng/mL), P3C (300 ng/mL), or OxPAPC (20 μg/mL) and RNA expression was measured. Commercially obtained OxPAPC activated IL-6 gene expression in WT and TLR2$^{-/-}$ mouse peritoneal macrophages, but not in cells from TLR4$^{-/-}$ mice (FIG. 9). TLR4-dependent cell activation by OxPAPC was substantially inhibited by Eritoran. Data are means+/−s.e.m. from 1 experiment with samples done in triplicate (*p<0.001, #p<0.05).

Figure 10A:
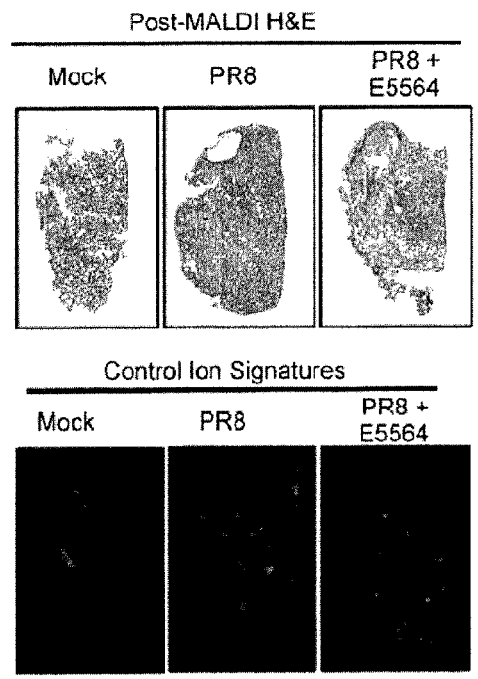
FIGS. 10A, 10B and 10C show eritoran treatment reduces the production of oxidized phospholipids following influenza infection.
Figure 10B:
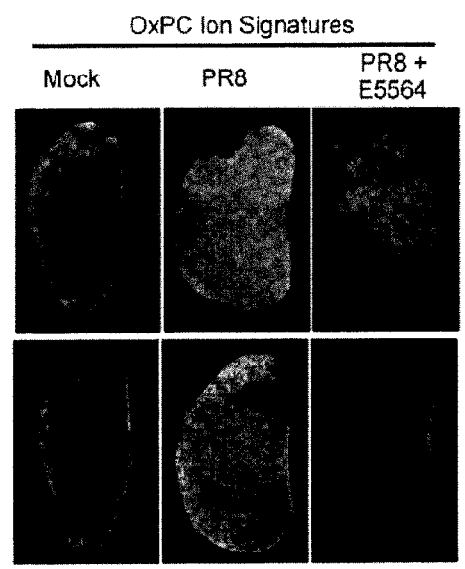
Figure 10C:
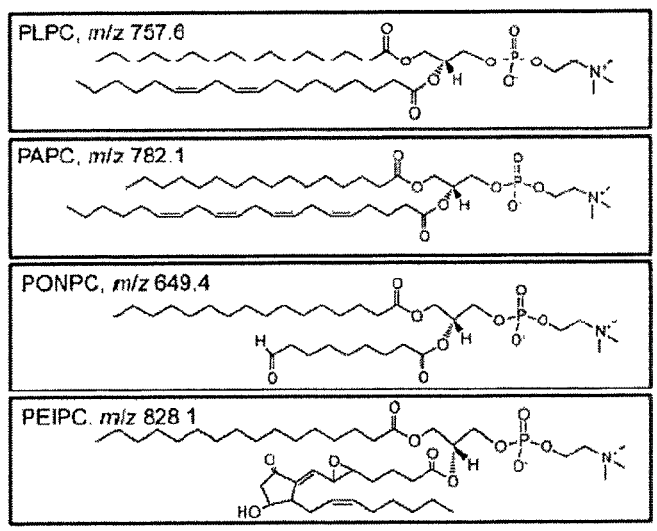

To assess the effect of eritoran on production of oxidized phospholipids during infection, MALDI-IMS was used to identify alterations in the lipid composition of mouse lungs after PR8, with or without eritoran treatment. Oxidation products were detected in greater abundance and intensity in PR8-infected versus mice that were treated with eritoran following infection or mock-infected mice. (FIG. 10a). Results are representative of 4 replicate experiments. The structures of abundant phosphatidylcholine (PC) and predicted oxidized phosphatidylcholine (OxPC) molecules and molecular weights: 1-palmitoyl-2-linoleoyl PC (PLPC) m/z 757.6, 1-palmitoyl-2-arachadonyl PC (PAPC) m/z 782.1, and predicted structures of oxidized PC molecules and molecular weight, 1-palmitoyl-2-(9-oxo)nonanoyl PC (PONPC) m/z 649.4, (PEIPC) 1-palmitoyl-2-(5,6-epoxyisoprostance E2 oyl) PC m/z 828.1 are shown. (FIG. 10b).

Eritoran is Not Directly Antiviral

TABLE 1

| | Titer (TCID$_{50}$/ml) |
|---|---|
| Experiment 1$^b$ | |
| Vehicle | 4.6 × 10$^6$ |
| E5564 treatment | 3.1 × 10$^6$ |
| E5564 pre-treatment | 1.0 × 10$^6$ |
| Experiment 2$^b$ | |
| Vehicle | 9.2 × 10$^5$ |
| E5564 treatment | 6.3 × 10$^6$ |
| E5564 pre-treatment | 3.4 × 10$^5$ |

As described above, eritoran treatment of influenza infected mice protected mice from influenza-induced lethality. To show that the protection was not caused by a direct effect of eritoran on virus replication, virus stocks of A/California/07/2009, H1N1 (titer of 10$^6$ TCID$_{50}$/mL) was titrated in MDCK cells with eritoran (10 ng/mL) or without eritoran (vehicle). Eritoran was applied 1 hour prior to or at the same time the virus was inoculated into the cell plate. Experiments 1 and 2 represent two independent experiments performed with two separate virus stocks.

Eritoran Fails to Protect PR8-Infected IFN-β Knockout Mice

Figure 11A:
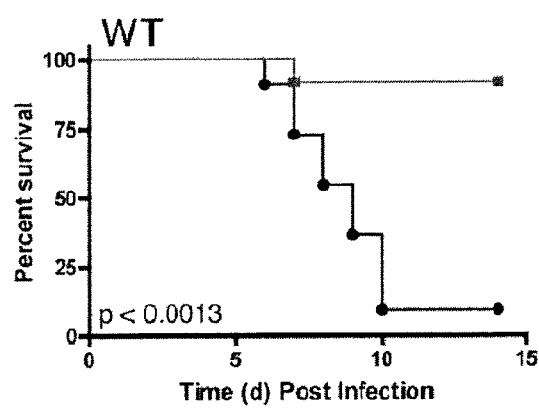
FIGS. 11A and 11B show eritoran fails to protect PR8-infected interferon-β knockout mice.
Figure 11B:
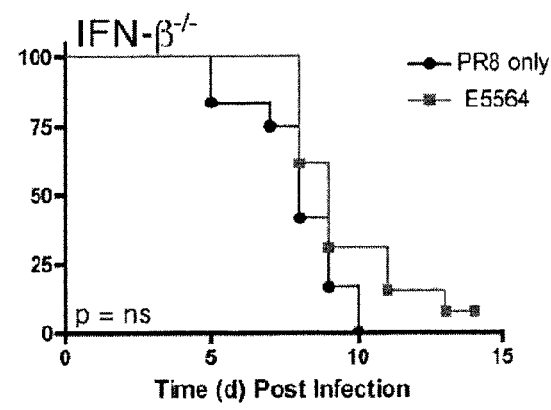

Eritoran treatment does not induce protection in PR8-infected IFNβ$^{-/-}$ mice. Wild-type and IFNβ$^{-/-}$ mice were infected with ~7500 TCID$_{50}$ PR8 and were left either untreated (circles) or treated with eritoran 2 days post-infection, for 5 successive days (squares). (FIG. 11). Data represent the combined results of 2 separate experiments (6 mice per treatment per experiment; WT: untreated vs. eritoran treatment (p<0.0013); IFNβ$^{-/-}$: untreated v. eritoran treatment (p=ns).

MD1 is Not an Alternative Target for Eritoran

Figure 12:
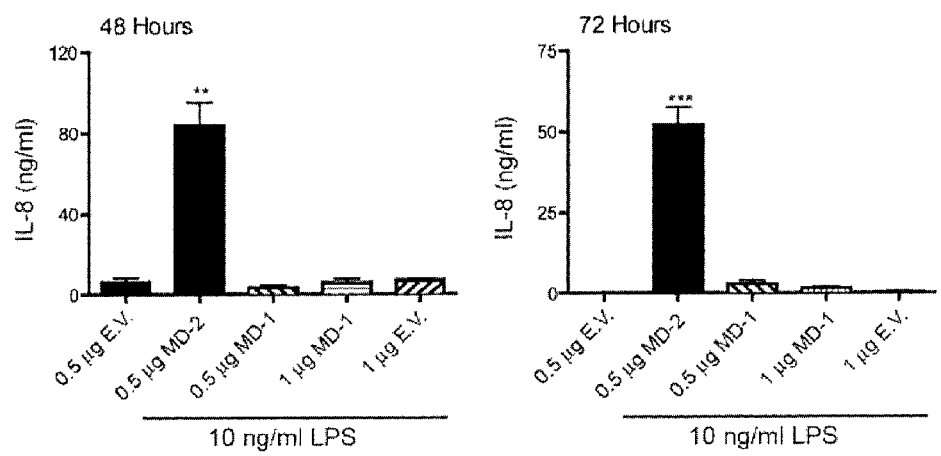
FIG. 12 shows MD1 is not an alternative target for eritoran.

MD-1 fails to substitute for MD-2 for LPS stimulation. HEK293 cells that stably express CD14 and TLR4 (HEK293-CD14-TLR4) were transfected with MD-2, MD-1 or empty vector (E.V.). (FIG. 12). At either 48 or 72 hours post-transfection, the cells were mock stimulated with PBS or stimulated with E. coli K235 LPS (10 ng/mL). Supernatants were collected 24 hours after stimulation and analyzed for total IL-8 levels by ELISA. Data represent mean and s.e.m. of cultures in a single experiment and represent an experimental n=3 (p<0.005, *p<0.001).

Molecular Requirements of Eritoran-Induced Protection

Figure 13A:
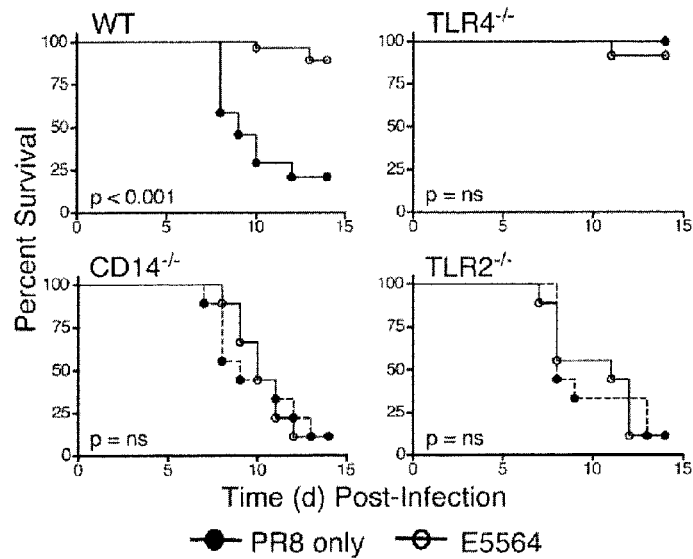
FIGS. 13A and 13B show the molecular requirements of eritoran-induced protection.

Normal mice (WT), TLR4$^{-/-}$, $^{TLR}$2$^{-/-}$, and CD14$^{-/-}$ were infected with influenza and then were untreated (closed circles) or treated with eritoran (open circles) 2 days post-infection, for 5 successive days. (FIG. 13a). As can be seen, influenza induce lethality was TLR4 dependent, but not CD14 or TLR2 dependent. In addition, eritoran treatment at 2 days post-infection was ineffective at inducing protection in either TLR2$^{-/-}$ or CD14$^{-/-}$ mice. WT data were combined from 5 separate experiments (5-6 mice per treatment per experiment), TLR4$^{-/-}$ data were combined from 3 separate experiments (5-6 mice per treatment per experiment), CD14$^{-/-}$ data were combined from 2 separate experiments (4-5 mice per treatment per experiment). WT: untreated vs eritoran (p, 0.0001); TLR4$^{-/-}$: untreated vs. eritoran (p=ns); CD14$^{-/-}$: untreated vs. eritoran (p=ns); TLR2$^{-/-}$: untreated vs. eritoran (p=ns).

Figure 13B:
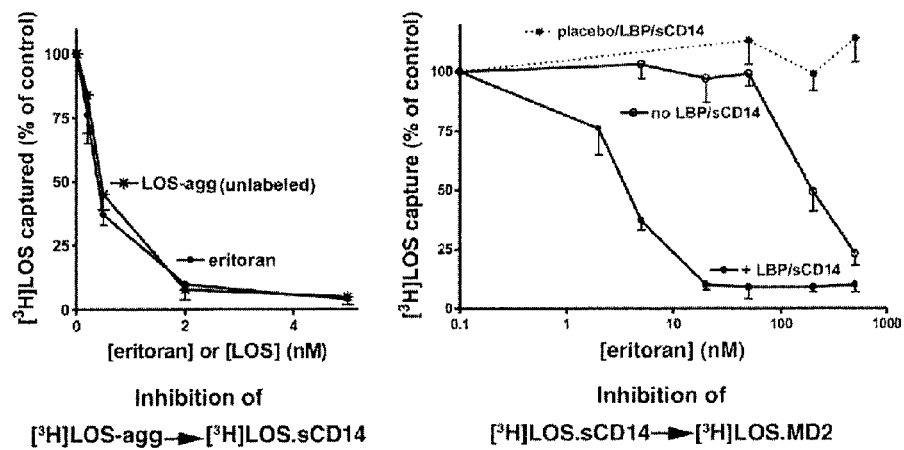

FIG. 13b shows the in vitro capacity of eritoran to bind CD14 and MD2, as measured by eritoran-mediated inhibition of LBP-dependent transfer of tritiated lipooligosaccharide ($^3$H-LOS; the LPS of Neisseria) to CD14 (FIG. 13b, left panel), as well as the transfer of $^3$H-LOS from CD14 to MD2 (FIG. 13b, right panel). Samples containing [$^3$H]LOS aggregates (0.2 nM), His6-sCD14 (~0.5 nM), and increasing concentrations as indicated of eritoran or unlabeled LOS (left panel) or 2 nM [$^3$H]LOS.sCD14, ca. 2 nM His6-MD2, and increasing concentrations of eritoran (or placebo)±LBP (50 pM) and sCD14 (2 nM) (right panel) were incubated for 30 min at 37° C., followed by addition and incubation with NiFF Sepharose beads to capture His-tagged proteins. Formation of complexes of [$^3$H]LOS with His6-sCD14 (left) or MD2 (right) was assayed by measuring co-capture of [$^3$H]LOS by NiFF Sepharose as previously described25. Data are expressed as percent of cocapture of [$^3$H]LOS observed in the absence of added eritoran. Results shown represent the mean±s.e.m. of 3 separate experiments with duplicate samples for each dose.

Statistics

Statistical differences between two groups were determined using an unpaired, two-tailed Student's t test with significance set at p<0.05. For comparisons between three or more groups, analysis was done by one-way ANOVA followed by a Tukey's multiple comparison test with significance determined at p<0.05.

The invention claimed is:

1. A method for treating a patient infected with influenza virus comprising: administering to the infected patient in need of said treatment a therapeutically effective amount of eritoran or a pharmaceutically acceptable salt thereof.

2. The method of claim 1 further comprising administering to the infected patient a therapeutically effective amount of an antiviral compound.

3. The method of claim 1, wherein the infected patient is administered a therapeutically effective amount of eritoran or a pharmaceutically acceptable salt thereof following testing positive for the presence of influenza infection.

4. The method of claim 3, wherein the infected patient tested for the presence of influenza infection using PCR, rt-PCR direct antigen detection tests, virus isolation in cell culture, or combinations thereof.

5. The method of claim 1, further comprising causing a decrease in influenza-induced cytokine mRNA levels in the infected patient.

6. The method of claim 5, further comprising causing a decrease in influenza-induced cytokine mRNA levels in the infected patient wherein the cytokines comprise TNF-α, IL-1β, IL-6, COX-2, IL-12 p40, KC, IL-10, IL-5, TGF-β or combinations thereof.

7. The method of claim 1, further comprising causing a decrease in influenza-induced interferon-beta or interferon gamma mRNA levels in the infected patient.

8. The method of claim 1, wherein the infected patient is administered a therapeutically effective amount of eritoran or a pharmaceutically acceptable salt thereof following the onset of clinical symptoms, wherein the clinical symptoms comprise cough, fever, pneumonia or combinations thereof.

9. The method of claim 1, wherein eritoran or a pharmaceutically acceptable salt thereof is administered by one of the routes comprising intravenous administration, intraperitoneal administration, intramuscular administration, intracoronary administration, intraarterial administration, intradermal administration, transdermal delivery, intratracheal administration, subcutaneous administration, intraarticular administration, intraventricular administration, inhalation, intracerebral, nasal, naval, oral, intraocular, pulmonary administration, impregnation of a catheter, by suppository and direct injection into a tissue, or systemically absorbed topical or mucosal administration.

10. The method of claim 9, wherein eritoran or a pharmaceutically acceptable salt thereof is administered intravenously.

11. The method of claim 1, wherein the effects of administering eritoran or pharmaceutically acceptable salts thereof cause a decrease in viral titers in the infected patient.

12. The method of claim 1, wherein the infected patient is administered a therapeutically effective amount of eritoran or a pharmaceutically acceptable salt thereof in a range of from between about 1 µg to about 240 mg, per dose.

13. A method for treating a patient infected with an orthomyxovirus comprising: administering to the infected patient in need of said treatment a composition comprising an active ingredient and a pharmaceutically acceptable carrier wherein the active ingredient comprises eritoran or a pharmaceutically acceptable salt thereof.

14. The method of claim 13, wherein the patient is infected with an orthomyxovirus selected from the group comprising influenza A, influenza B, influenza C or combinations thereof.

15. The method of claim 13, further comprising administering to the infected patient a therapeutically effective amount of an antiviral compound.

16. The method of claim 13, wherein the infected patient is administered a therapeutically effective amount of eritoran or a pharmaceutically acceptable salt thereof following testing positive for the presence of influenza infection.

17. The method of claim 16, wherein the infected patient tested for the presence of influenza infection using PCR, rt-PCR direct antigen detection tests, virus isolation in cell culture, or combinations thereof.

18. The method of claim 13, further comprising causing a decrease in influenza-induced cytokine mRNA levels in the infected patient.

19. The method of claim 18, further comprising causing a decrease in influenza-induced cytokine mRNA levels in the infected patient wherein the cytokines comprise TNF-α, IL-1β, IL-6, COX-2, IL-12 p40, KC, IL-10, IL-5, TGF-β or combinations thereof.

20. The method of claim 13, further comprising causing a decrease in influenza-induced interferon-beta or interferon gamma mRNA levels in the infected patient.

21. The method of claim 13, wherein the infected patient is administered a therapeutically effective amount of eritoran or a pharmaceutically acceptable salt thereof following the onset of clinical symptoms, wherein the clinical symptoms comprise cough, fever, pneumonia or combinations thereof.

22. The method of claim 13, wherein eritoran or a pharmaceutically acceptable salt thereof is administered by one of the routes comprising intravenous administration, intraperitoneal administration, intramuscular administration, intracoronary administration, intraarterial administration, intradermal administration, transdermal delivery, intratracheal administration, subcutaneous administration, intraarticular administration, intraventricular administration, inhalation, intracerebral, nasal, naval, oral, intraocular, pulmonary administration, impregnation of a catheter, by suppository and direct injection into a tissue, or systemically absorbed topical or mucosal administration.

23. The method of claim 22, wherein eritoran or a pharmaceutically acceptable salt thereof is administered intravenously.

24. The method of claim 13, wherein the effects of administering eritoran or pharmaceutically acceptable salts thereof cause a decrease in viral titers in the infected patient.

25. The method of claim 13, wherein the infected patient is administered a therapeutically effective amount of eritoran or a pharmaceutically acceptable salt thereof in a range of from between about 1 µg to about 240 mg, per dose.

26. A method for mitigating influenza-induced lung pathology, cytokine production, liver enzyme levels, and/or oxidized host phospholipids in an infected patient comprising: administering to the infected patient in need of said mitigation a therapeutically effective amount of a TLR4 antagonist, wherein the TLR4 antagonist comprises eritoran or a pharmaceutically acceptable salt thereof.

27. The method of claim 26, further comprising administering to the infected patient a therapeutically effective amount of an antiviral compound.

28. The method of claim 26, wherein the infected patient is administered a therapeutically effective amount of eritoran or a pharmaceutically acceptable salt thereof following testing positive for the presence of influenza infection.

29. The method of claim 28, wherein the infected patient tested for the presence of influenza infection using PCR, rt-PCR direct antigen detection tests, virus isolation in cell culture, or combinations thereof.

30. The method of claim 26, further comprising causing a decrease in influenza-induced cytokine mRNA levels in the infected patient.

31. The method of claim 30, further comprising causing a decrease in influenza-induced cytokine mRNA levels in the infected patient wherein the cytokines comprise TNF-α, IL-1β, IL-6, COX-2, IL-12 p40, KC, IL-10, IL-5, TGF-β or combinations thereof.

32. The method of claim 26, further comprising causing a decrease in influenza-induced interferon-beta or interferon gamma mRNA levels in the infected patient.

33. The method of claim 26, wherein the infected patient is administered a therapeutically effective amount of eritoran or a pharmaceutically acceptable salt thereof following the onset of clinical symptoms, wherein the clinical symptoms comprise cough, fever, pneumonia or combinations thereof.

34. The method of claim 26, wherein eritoran or a pharmaceutically acceptable salt thereof is administered by one of the routes comprising intravenous administration, intraperitoneal administration, intramuscular administration, intracoronary administration, intraarterial administration, intradermal administration, transdermal delivery, intratracheal administration, subcutaneous administration, intraarticular administration, intraventricular administration, inhalation, intracerebral, nasal, naval, oral, intraocular, pulmonary administration, impregnation of a catheter, by suppository and direct injection into a tissue, or systemically absorbed topical or mucosal administration.

35. The method of claim 34, wherein eritoran or a pharmaceutically acceptable salt thereof is administered intravenously.

36. The method of claim 26, wherein the effects of administering eritoran or pharmaceutically acceptable salts thereof cause a decrease in viral titers in the infected patient.

37. The method of claim 26, wherein the infected patient is administered a therapeutically effective amount of eritoran or a pharmaceutically acceptable salt thereof in a range of from between about 1 µg to about 240 mg, per dose.

* * * * *